United States Patent
Kasai et al.

(10) Patent No.: US 7,189,219 B1
(45) Date of Patent: Mar. 13, 2007

(54) ABSORBENT ARTICLE

(75) Inventors: Takao Kasai, Tochigi (JP); Kazuyuki Maeda, Tochigi (JP); Taketo Itoh, Tochigi (JP)

(73) Assignee: Kao Corporation, Tokyo (JP)

( * ) Notice: Subject to any disclaimer, the term of this patent is extended or adjusted under 35 U.S.C. 154(b) by 259 days.

(21) Appl. No.: 10/049,828

(22) PCT Filed: Nov. 2, 2000

(86) PCT No.: PCT/JP00/07754

§ 371 (c)(1),
(2), (4) Date: Feb. 19, 2002

(87) PCT Pub. No.: WO01/34083

PCT Pub. Date: May 17, 2001

(30) Foreign Application Priority Data

Nov. 10, 1999 (JP) .................................. 11-320340

(51) Int. Cl.
A61F 13/15 (2006.01)
A61F 13/20 (2006.01)

(52) U.S. Cl. ............................. 604/385.28; 604/385.24

(58) Field of Classification Search ........... 604/385.01, 604/385.24–385.28, 386–389
See application file for complete search history.

(56) References Cited

U.S. PATENT DOCUMENTS

| 4,015,604 A | 4/1977 | Csillag |
| 4,200,103 A | 4/1980 | Black et al. |
| 4,738,677 A * | 4/1988 | Foreman ................. 604/385.27 |
| 4,743,246 A | 5/1988 | Lawson |
| 4,795,454 A | 1/1989 | Dragoo |
| 5,662,637 A * | 9/1997 | Kitaoka et al. ......... 604/385.28 |
| 5,669,896 A * | 9/1997 | Kielpikowski .......... 604/385.28 |
| 5,762,642 A | 6/1998 | Coles et al. |
| H1746 H | 8/1998 | Carrier et al. |
| 2002/0138061 A1 * | 9/2002 | Nakaoka et al. ........ 604/385.28 |

FOREIGN PATENT DOCUMENTS

| EP | 0 263 720 B1 | 4/1988 |
| EP | 0 264 238 A1 | 4/1988 |
| JP | 63-182401 | 7/1988 |

* cited by examiner

*Primary Examiner*—Michele Kidwell
(74) *Attorney, Agent, or Firm*—Birch, Stewart, Kolasch & Birch, LLP

(57) ABSTRACT

An absorbent article comprises a liquid-permeable topsheet, a liquid-impermeable backsheet and a liquid-retentive absorbent core interposed between the topsheet and the backsheet. The absorbent article is substantially vertically elongated and has an upstanding gather. The topsheet has a liquid shut-off region in a line shape and adapted to prohibit migration of a liquid in the topsheet. The liquid shut-off region is formed at a region outside a peripheral edge portion but other than a joined section between the topsheet and a sheet material for forming the upstanding gather.

5 Claims, 3 Drawing Sheets though this application is the national phase under 35 U.S.C. § 371 of PCT International Application No. PCT/JP00/07754 which has an International filing date of Nov. 2, 2000, which designated the United States of America and was published in English.

ABSORBENT ARTICLE

This application is the national phase under 35 U.S.C. § 371 of PCT International Application No. PCT/JP00/07754 which has an International filing date of Nov. 2, 2000, which designated the United States of America and was published in English.

TECHNICAL FIELD

The present invention relates to an absorbent article such as a disposable diaper which is excellent in anti-leak properties.

BACKGROUND ART

In a conventional disposable diaper, it sometimes occurs that a discharged body liquid migrates through the interior of a topsheet under the effect of capillary action and reaches a peripheral edge portion with a result of leakage therefrom. As a technique for preventing the leak of a liquid from the opposite side edge portions in the longitudinal direction of the diaper, Japanese Patent Application Laid-open No. 63-182401 proposes a diaper in which a sheet material for forming an upstanding gather and a topsheet are joined together at an upper part of an absorbent core and the leak of a body liquid from opposite side edge portions of the diaper is restrained by utilizing the joined section (or junction).

However, since the topsheet of this diaper is designed such that its end portion does not reach an end portion of the product and joining means for joining the upstanding gather serves as leak restraining means, the processing conditions for joining a plurality of sheets are limited. Moreover, in the case where an adhesive agent is used as means for joining the upstanding gather and the topsheet together, in the case where the topsheet is a bulky nonwoven fabric, a large amount of adhesive agent must be used for the adhesion thereof and for the restraint of leak thereof, thus resulting in problems of impairment of flexibility and increase in manufacturing cost. Moreover, in the case where a continuous production is to be performed, the topsheet must be arranged intermittently in a direction of the flow of a raw fabric, thus resulting in serious deterioration in productivity. In addition, the anti-leak effect is not sufficient, as well.

DISCLOSURE OF THE INVENTION

It is, therefore, an object of the present invention to provide an absorbent article which is good in workability (or processibility), which can exhibit a satisfactory anti-leak effect even when a bulky topsheet is employed, which is good in productivity and which is low in manufacturing cost.

The present invention has achieved the above object by providing an absorbent article including a liquid-permeable topsheet, a liquid-impermeable backsheet and a liquid-retentive absorbent core interposed between the topsheet and the backsheet, the absorbent article being substantially vertically elongated and having an upstanding gather, wherein the topsheet has a liquid shut-off region in a linear shape which prevents liquid migration within the topsheet, and the liquid shut-off region is located at an area outside the periphery of the absorbent core and is formed independent of a joined section between the topsheet and a sheet material for forming the upstanding gather.

BEST MODE FOR CARRYING OUT THE INVENTION

Figure 1:
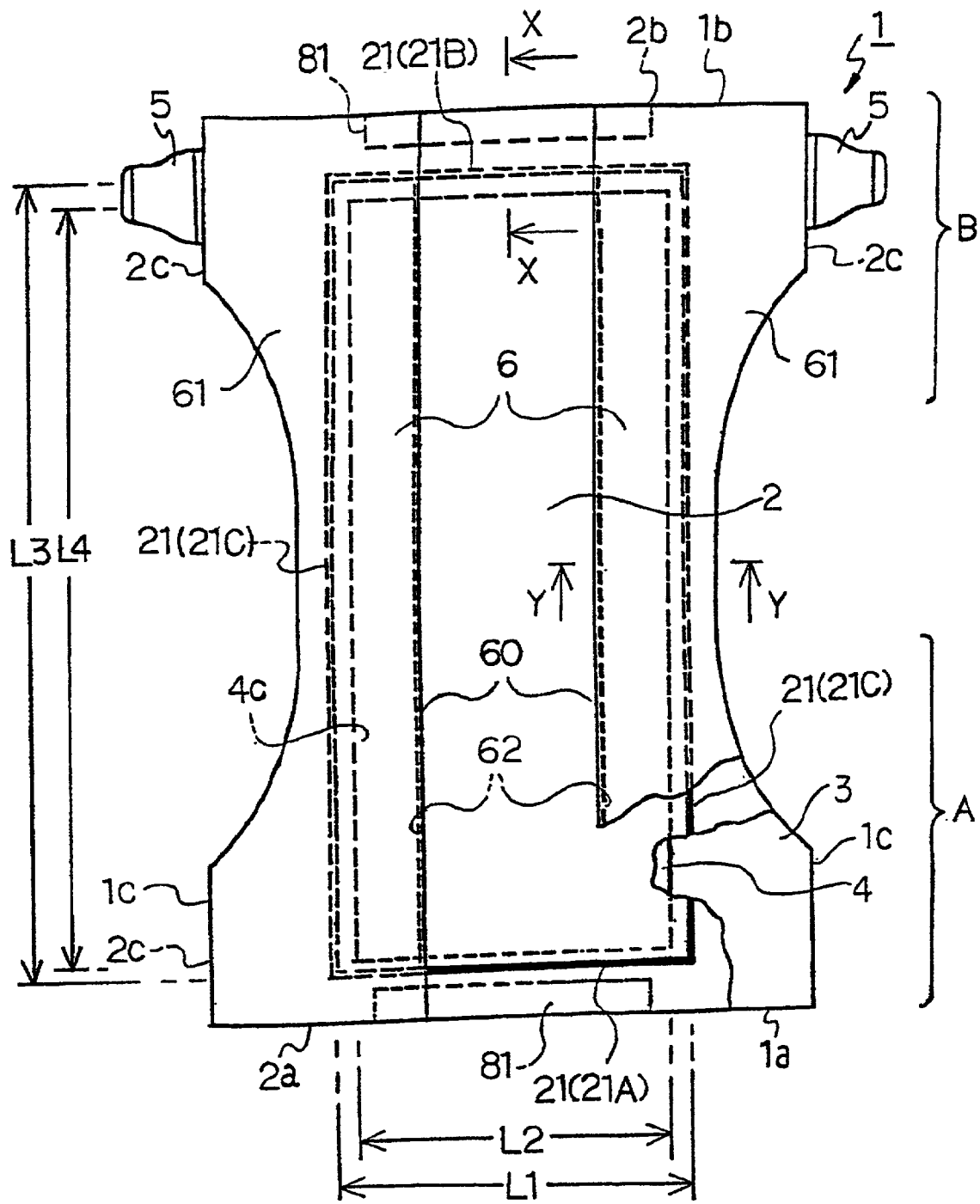
FIG. 1 is a plan view, when viewed from a topsheet side, showing one state of a disposable diaper according to one embodiment of the present invention, in which an elastic member is in a stretched position.

An preferred embodiment of the present invention will be described hereinafter. A disposable diaper 1 as an absorbent article in this embodiment is a so-called flat-type disposable diaper including a liquid-permeable topsheet 2, a liquid-impermeable backsheet 3 and a liquid-retentive absorbent core 4 interposed between the topsheet 2 and the backsheet 3, the disposable diaper 1 being substantially vertically elongated and having a pair of left and right fastening tapes 5, 5 at opposite side edge portions of its back side B.

The topsheet 2 and the backsheet 3 each have a vertically elongated configuration and joined together at a peripheral edge portion extending outward beyond the absorbent core 4. The absorbent core 4 has a vertically elongated configuration and it is fixedly sandwiched between the topsheet 2 and the backsheet 3. Opposite end edges 2*a*, 2*b* of the topsheet 2 in the longitudinal direction of the diaper 1 and opposite left and right side edges 2*c*, 2*c* of the topsheet 2 in the longitudinal direction of the diaper 1 are extended to opposite end edges 1*a*, 1*b* and opposite side edges 1*c*, 1*c* of the diaper 1, respectively. On opposite side regions in the longitudinal direction of the diaper 1, sheet materials 61, 61 for forming upstanding gathers are arranged to form a pair of left and right upstanding gathers 6, 6.

Figure 3:
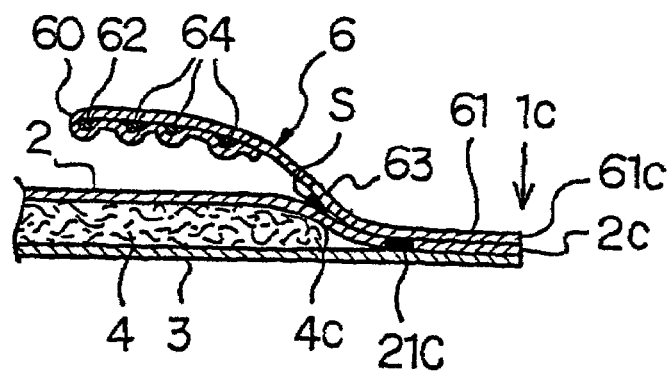
FIG. 3 is a sectional view taken on line Y—Y of FIG. 1.

As shown in FIG. 3, the sheet material 61 for forming the upstanding gather is disposed inward of the diaper from each side edge in the longitudinal direction of the diaper. An elastic member 62 is fixed, in its stretched state, to a free end portion 60 on the widthwise center side of the disposable diaper 1 along an end edge of the free end portion 60. The sheet material 61 is secured to an upper part of each side portion 4*c* of the absorbent core 4 by thermal-fusing or adhesive agent. By the joining of the sheet material 61 to the upper part of each side portion, a basal end 63 of the upstanding gather 6 is formed. Each sheet material 61 extends outward beyond each side edge portion 4*c* in the longitudinal direction of the absorbent core 4 so that a side edge 61*c*, which is located on the other side of the side edge portion forming the free end portion 60, is located at the side edge 1*c* of the diaper 1. The sheet material 61 is in intimate contact with the topsheet 2 at its extended section. A plurality of elastic members 64, 64, as shown in FIG. 3, are fixedly arranged, in their stretched states and in parallel with the elastic member 62, between the elastic member 62 and the basal end 63 in each sheet 61.

Waist portion elastic members 81, 81 for forming waist gathers are disposed at opposite end portions in the longitudinal direction of the disposable diaper 1 but the upstanding gathers are not formed thereon.

The topsheet 2 of the disposable diaper 1 has a liquid shut-off region 21 in a linear shape which prevents liquid migration within the topsheet 2. The expression "in a linear shape" used herein refers to a line effective for restraining the penetration of a body liquid but it does not necessarily mean that the seal lines, etc. are continuously formed without interruption. For example, if intermittent seal lines placed one upon another and arranged in array can prohibit the migration of a body liquid within the topsheet 2, this arrangement can be said as "in a linear shape". The concept of the expression "in a linear shape" includes not only a straight-line shape but also a curved-line shape and a bent-line shape. The width of the line is preferably about 0.5 to 15 mm. The liquid shut-off regions 21 are located on the opposite longitudinal end portions and the opposite side portions of the diaper 1. The liquid shut-off regions 21A, 21B located on the longitudinal end portions, respectively, are in a linear shape over the widthwise direction of the diaper 1, whereas the liquid shut-off regions 21C, 21C located on the side portions, respectively, are in a linear shape over the longitudinal direction of the diaper 1.

More specifically, the liquid shut-off regions 21A, 21B of the opposite end portions in the longitudinal direction of the diaper 1 are formed over a region between the opposite side edges of the absorbent core 4 along the opposite end edges of the absorbent core 4, whereas the opposite left and right liquid shut-off regions 21C, 21C are formed over a region between the opposite end edges of the absorbent core 4 along the opposite left and right side edges of the absorbent core 4. In the case where the liquid shut-off regions 21A, 21B are formed on the regions outside the end edges in the longitudinal direction of the absorbent core 4 (the same direction as the longitudinal direction of the absorbent article), the lengths L1 (only one is shown) of the liquid shut-off regions 21A, 21B are preferably larger than 100% of the length L2 (only one is shown) of the opposite end edges of the absorbent core 4 and terminated in the product. In the case where the liquid shut-off regions 21C, 21C are formed on the regions outside the side edges in the longitudinal direction of the absorbent core 4, the lengths L3 (only one is shown) of the liquid shut-off regions 21C, 21C are preferably larger than 100% of the length L4 (only one is shown) of the opposite side edges of the absorbent core 4 and terminated in the regions inside the opposite ends 1a, 1b in the longitudinal direction of the product.

In this embodiment, the liquid shut-off regions 21A, 21B and the liquid shut-off regions 21C, 21C are mutually connected together at areas in the vicinity of the four corner portions of the absorbent core 4. The absorbent core 4 is surrounded with the liquid shut-off region 21 at area outside its peripheral edge portion over the entire periphery. In this embodiment, each liquid shut-off region 21 is generally a straight line.

Each liquid shut-off region 21 is formed at a region outside the peripheral edge portion of the absorbent core 4. That is to say, the liquid shut-off regions 21A, 21B are formed at regions outside the opposite end edges in the longitudinal direction of the absorbent core 4, whereas the liquid shut-off regions 21C, 21C are formed at regions outside the opposite left and right side edges in the longitudinal direction of the absorbent core 4. Owing to this feature, even if a body liquid should migrate through the interior of the topsheet, the body liquid would not leak from the peripheral edge portion of the diaper because it would collide against any or some of the liquid shut-off regions so that further movement of the body liquid is prohibited. That is to say, the leak of a body liquid from the waist portion is prevented by the liquid shut-off regions 21A, 21B and the leak from the leg areas is likewise prevented by the liquid shut-off regions 21C, 21C.

In the disposable diaper 1 of this embodiment, since the liquid shut-off regions 21A, 21B are formed on the opposite end portions in the longitudinal direction of the diaper over the widthwise direction of the diaper, a similar anti-leak effect to one having a waist upstanding gather can be obtained nevertheless it has no waist upstanding gather.

Figure 2:
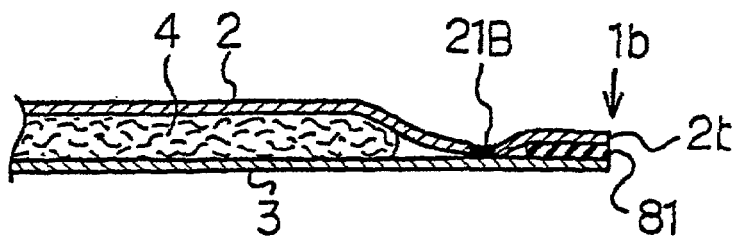
FIG. 2 is a sectional view taken on line X—X of FIG. 1.

As shown in FIGS. 2 and 3, the respective liquid shut-off regions 21 are formed independent of a joined section S between the topsheet 2 and the sheet material 61 for forming the upstanding gather. That is to say, the respective liquid shut-off regions 21 are formed at other regions than a joined section S between the topsheet 2 and the sheet material 61. The liquid shut-off regions 21 are not formed at the time the sheet material 6 for forming the upstanding gather is joined to the topsheet 2.

Figure 4:
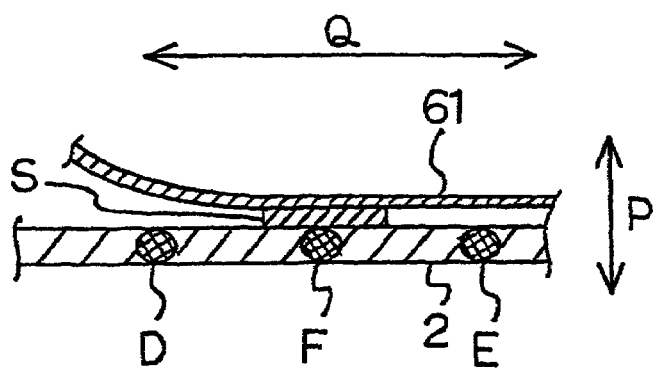
FIG. 4 is an explanatory view for explaining the location where a liquid shut-off region is formed.

The expression "joined section" between the topsheet and the sheet material for forming the upstanding gather used herein refers to an adhesive layer and a hot-melt layer which are formed between the topsheet and the sheet material for forming the upstanding gather when the topsheet and the sheet material are joined together. As a material for forming the adhesive layer, there can be listed an adhesive agent such as a hot-melt. The hot-melt layer is formed on an interface between the topsheet and the sheet material for forming the upstanding gather by applying a heat-seal, an ultrasonic-seal or the like to the sheet material and the topsheet to melt a part of the sheet material and/or the topsheet. The expression "the liquid shut-off region is formed independent of a joined section" means not only a case that the liquid shut-off region and the "joined section" as defined above are not overlapped with each other when the diaper is viewed in the sectional direction (indicated by an arrow P in FIG. 4), but also a case that the liquid shut-off region and the "joined section" are not overlapped with each other when the diaper is viewed in the horizontal direction (indicated by an arrow Q in FIG. 4). The liquid shut-off region in the present invention includes, for example, those in which the liquid shut-off region as indicated by D and E of FIG. 4 is not overlapped with the joined section S when the absorbent article is viewed not only in a plan view but also in the sectional direction. It also includes, for example, those in which the liquid shut-off region as indicated by F of FIG. 4 is overlapped with the joined section S when the absorbent article is viewed in a plan view but the liquid shut-off region is not overlapped with the joined section S when the absorbent article is viewed in a sectional direction (see FIG. 4) in the widthwise direction thereof. Embodiments for forming the liquid shut-off region independent of the joined section include (1) forming the joined section by using an adhesive while forming the liquid shut-off region by the other means than that of the joined section such as a heat-seal and an ultrasonic-seal, and (2) forming the both by the same means but making the both differ in the position to be formed in the extending direction of the sheet material for forming the upstanding gather. Since the liquid shut-off region is for preventing a body liquid from leaking out due to the liquid migration within the topsheet, it is preferably formed over the entire width dimension of the topsheet. FIG. 4 shows a joined section (adhesive layer) S formed by joining the sheet material 61 for forming the upstanding gather to the topsheet through an adhesive agent.

By forming the liquid shut-off region 21 to be independent of the joined section between the sheet material 61 and the topsheet 2, the working (or processing) conditions required at the time of joining the sheet material 61 for forming an upstanding gather are not limited, the sheet material 61 can be joined to the topsheet 2 by an appropriate method even in the case where a bulky nonwoven fabric is used for the topsheet 2.

It is preferable that the liquid shut-off region 21 in the present invention be formed independent of a joined section between the topsheet 2 and other sheets (sheet material 61, backsheet 3, etc.).

Accordingly, the diaper 1 can be manufactured economically. The topsheet 2 in this embodiment is not thermally bonded to other sheet materials (the sheet material 61 and the backsheet 3) at the respective liquid shut-off regions 21. The bulky topsheet is a sheet manufactured, for example, by an air-laid, air-through system. It has a basis weight of 20 g/m2 or more, preferably 25 g/m2 or more and a thickness of 0.3 mm or more, preferably 0.6 mm or more.

According to this diaper 1, since the opposite end edges 2a, 2b of the topsheet 2 extends to the opposite end edges 1a, 1b of the diaper 1, it is not necessary to intermittently arrange the topsheets 2 in the case where diapers are continuously manufactured with the longitudinal direction of the diaper serving as a flow direction. Moreover, since the opposite side edges 2c, 2c of the topsheet 2 are extended to the opposite side edges 1c, 1c of the diaper 1, it is not necessary to intermittently arrange the topsheets 2 even in the case where the widthwise direction of the diaper serves as a flow direction.

The liquid shut-off region 21 in this embodiment is formed by heat seal.

That is to say, the topsheet 2 is a sheet of nonwoven fabric which comprises a thermally fusible material, more particularly is composed of a thermally fusible synthetic fiber. Each liquid shut-off region 21 is formed by pressing a heat-seal material such as a heat roll against the sheet so as to melt a part of the sheet. In the case where the liquid shut-off region is formed by heat seal, the seal width is preferably 0.2 to 15 mm and particularly preferably 0.5 to 5 mm from the view point of strength, liquid shut-off property and high productivity.

Moreover, in this disposable diaper 1, as shown in FIG. 3, the liquid-permeable topsheet 2, which covers the skin contacting surface (that surface which is faced with the wearer's skin side) of the absorbent core 4, extends outward (outward in the widthwise direction) beyond the basal ends 63 of the upstanding gathers 6 form on the opposite side portions in the longitudinal direction of the diaper, and at least a part of the extended section (the same direction as the widthwise direction of the diaper) of the topsheet 2a extending outward beyond the basal ends is joined to the backsheet through an adhesive agent, not shown. The two liquid shut-off regions 21C are each formed on the extended topsheet 2a which extend outward beyond the basal ends 63 of the upstanding gathers.

In this diaper 1, since the extended section 2a of the liquid-permeable topsheet 2 is present at the back side of that portion of the sheet material 61 for forming an upstanding gather which is located outside the basal end 63 in the widthwise direction, a good moisture absorbing property can be obtained at opposite side portions of the diaper even in the case where a hydrophobic sheet material is used as the sheet material 61 for forming an upstanding gather, thus enabling to prevent the generation of heat rash.

Moreover, in this diaper 1, the sealing between the sheet material 61 and the backsheet 3 at opposite side portions of the diaper is achieved by the adhesive agent for joining the sheet material 61 for forming an upstanding gather and the topsheet 2 together, the liquid shut-off regions 21C formed on the top sheet 2 and the adhesive agent for joining the topsheet 2 and the backsheet 3 together. Owing to this feature, the feeling at the opposite side portions of the diaper is not degraded and the backsheet 3 is not damaged, either.

Figure 5A:
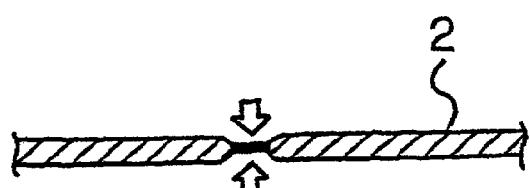
FIG. 5(*a*) is an illustration showing one example of a method for forming a liquid shut-off region, and FIG. 5(*b*) is an illustration showing another example thereof.
Figure 5B:
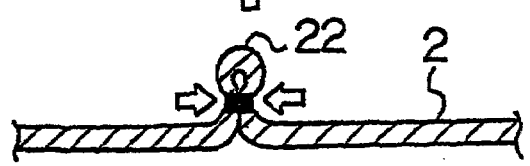

This diaper 1 can easily be manufactured by preliminarily forming the respective liquid shut-off regions 21 on the topsheet 2 and then arranging the topsheet 2 with the liquid shut-off regions 21 formed thereon at a predetermined location of the diaper 1. This manufacturing method is one embodiment of a method for manufacturing an absorbent article of the present invention. As a method for forming the liquid shut-off regions, the liquid shut-off regions 21A to 21C may all be formed simultaneously using a single heat-seal member or after the liquid shut-off regions 21A, 21B are formed by a single heat-seal member, the liquid shut-off members 21C, 21C may be formed by another heat-seal member. This order may be reversed. Moreover, the liquid shut-of region 21A and the liquid shut-off region 21B, and both the liquid shut-off regions 21C, 21C may be formed using different heat seal members, respectively. In the case where the liquid shut-off regions are formed by heat-seal, the topsheet may be sandwiched between and pressed by the heat-seal members from the opposite surfaces as shown in FIG. 5(*a*). It is also accepted that the topsheet 2 is folded back and the folded-back portion 22 is sandwiched between and pressed by the heat seal members from the opposite sides as shown in FIG. 5(*b*).

The diaper 1 of this embodiment can be manufactured by arranging the topsheet 2 with the liquid shut-off regions 21A, 21B, 21C, 21C formed thereon at a predetermined location in the diaper 1 so that the liquid shut-off regions 21A, 21B, 21C, 21C are arranged at the locations as shown in FIGS. 1 to 3, respectively. By preliminarily forming the liquid shut-off regions 21 on the topsheet 2 and then arranging the topsheet with the liquid shut-off regions 21 formed thereon at a predetermined location as just mentioned, a wide variety of joining methods can selectively be used when the sheet material 61 for forming an upstanding gather is joined to the topsheet 2. Hence, the best joining method can be selected taking into consideration the economical efficiency, etc. By this, the productivity of a diaper is enhanced and an economically efficient manufacture can be obtained. It should be noted that those points, which are not particularly described in this embodiment, are the same as in the conventional method for manufacturing a diaper.

It is necessary that the liquid shut-off regions are formed in such a manner as to be able to prohibit the migration of a body liquid through the interior of the topsheet. In the case where a nonwoven fabric is used for the topsheet and the liquid shut-off regions are formed by heat-sealing the nonwoven fabric, it is preferred that they are processed at a temperature of the melt point (m. p.) of the component fiber of the nonwoven fabric or higher and it is more preferable that they are processed at a temperature of the melt point plus 20° C. or higher. It is also effective to use a fiber of a core-sheath structure as the component fiber in order to maintain the strength of the nonwoven fabric. In that case, it is preferable that a resin having a high melt point is used as the core, a resin having a low melt point is used as the sheath and they are processed at temperatures equal to or higher than the melt point of the sheath component but lower than the melt point of the core component. For example, in the case where the core fiber is PET and the sheath component is PE, sealing is performed at temperatures equal to or higher than 130° C. at which the sheath component is melted, but lower than 230° C. at which the core component PET is melted.

A nonwoven fabric is preferable as the material for forming the topsheet 2 as mentioned above. As the materials for forming the backsheet 3, the absorbent core 4, the sheet material 61 for forming an upstanding gather, the elastic members 62, 64, 81 and the fastening tape 5, those, which are normally used for a disposable diaper, can be used without any particular limitation. For example, as the sheet material 61 for forming an upstanding gather, there can be used a spunbond, a spunbond/meltblown/spunbond, a spunbond/meltblown/meltblown/spunbond, an airthrough nonwoven fabric and the like. Particularly preferably, they have hydrophobic properties.

Figure 6:
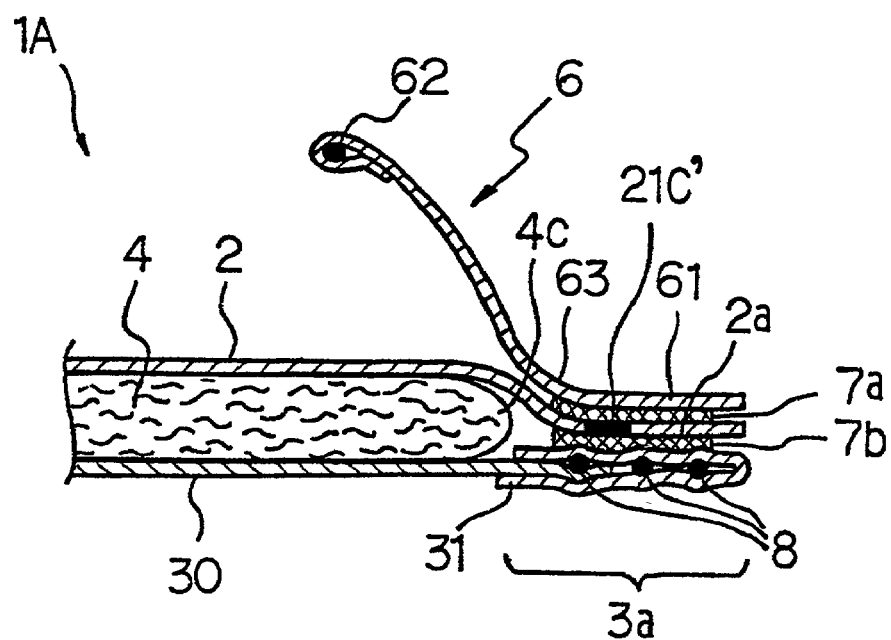
FIG. 6 is a sectional view (corresponding to FIG. 3) showing a disposable diaper according to another embodiment of the present invention.
Figure 7:
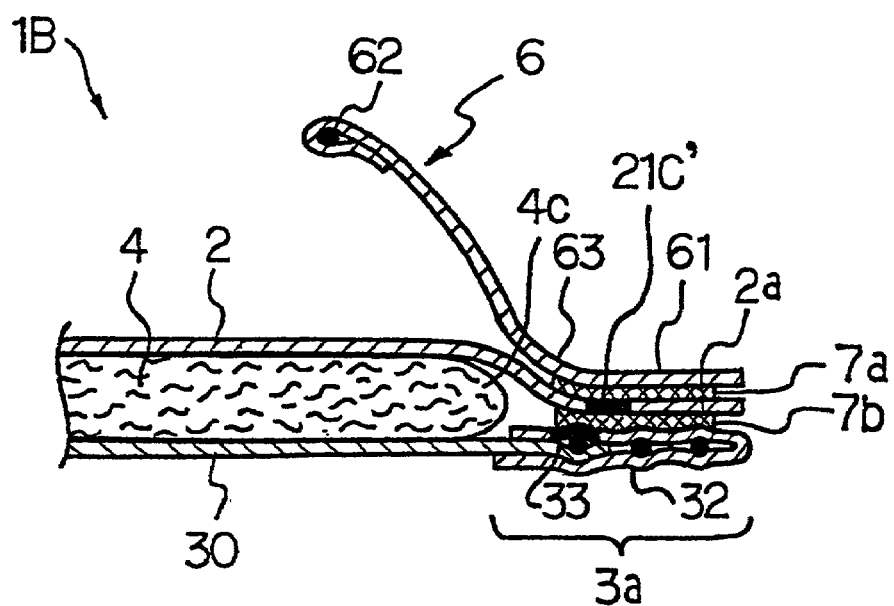
FIG. 7 is a sectional view (corresponding to FIG. 3) showing a disposable diaper according to a further embodiment of the present invention.

A disposable diaper according to another embodiment of the present invention will be described next. FIGS. 6 and 7 are illustrations, which correspond to FIG. 3, each showing a sectional view in the widthwise direction of a disposable diaper according to another embodiment of the present invention. Those points of the disposable diapers shown in FIGS. 6 and 7, which are not particularly described, are the same as the above-mentioned disposable diaper 1 and the description on the above-mentioned disposable diaper 1 is applicable thereto, where appropriate.

In a disposable diaper 1A shown in FIG. 6, a hydrophobic sheet material 31 is adhesively laminated on that section of the sheet material 30 for forming a backsheet which covers a skin non-contacting side of an absorbent core 4, which extends outward in the widthwise direction from each side edge 4c of the absorbent core 4, and opposite side portions 3a of a backsheet 3 is composed of those sheet materials 30, 31, thereby exhibiting a dual layer structure. An outward extended topsheet 2a from a basal end 63 of an upstanding gather 6 is joined to the opposite side portions 3a exhibiting a dual structure in the backsheet 3. An outward extended backsheet 2a from the basal end 63 of the upstanding gather 6 is formed with a liquid shut-off regions 21C' which is similar to the liquid shut-off region 21C of the disposable diaper 1. In this disposable diaper 1A, the sealing between the top and bottom surfaces at the opposite side portions of the diaper is achieved by an adhesive agent for joining the sheet material 61 for forming an upstanding gather and the topsheet 2 together, the liquid shut-off region 21C' formed on the topsheet 2, and an adhesive agent 7b for joining the topsheet 2 and the backsheet 3 together. The upstanding gather 6 in this disposable diaper 1A includes only a single elastic member 62. In FIG. 6, reference numeral 8 denotes an elastic member for forming a leg gather.

A disposable diaper 1B shown in FIG. 7 is different from the disposable diaper 1A only in the respect that the former includes, instead of the hydrophobic sheet material 31 in the disposable diaper 1A of FIG. 6, a hydrophilic sheet material 32 having a liquid shut-off region 33 which is similar to the liquid shut-off region 21C'. The opposite side portions 3a of the backsheet 3 in this disposable diaper 1B comprises a sheet material 30 extending outward in the widthwise direction beyond opposite side edges 4c of the absorbent core 4 and the sheet material 32 adhesively laminated on the sheet material 30. According to the disposable diapers 1A, 1B shown in FIGS. 6 and 7, there can be exhibited the similar effect to that of the disposable diaper 1.

The present invention should not be limited to the above embodiments. For example, although a method for forming the liquid shut-off region on the topsheet is preferably a heat-seal, it may be an ultrasonic seal. Or otherwise, the liquid shut-off region may be formed on the topsheet by sufficiently impregnating a thermoplastic resin, a wax, a hot-melt, a foamed body having a closed cell, a resin plasticized by water, a water-absorptive polymer or the like into fiber voids of the nonwoven fabric. Among them, the hot-melt is preferable and particularly preferably a hot-melt having less tackiness (in blending of the hot-melt, the molecular weight of the base resin is high and the blending ratio is high). The coating quantity of the hot-melt is preferably 20 to 100 g/m2, and the coating system is preferably in the form of a plane or a bead using a coater. The kinds of usable hot-melt are not particularly limited. A styrene-based hot-melt, an olefin-based hot-melt, a solvent, a viscous agent, an aqueous tacky agent, or the like can be used.

In the above embodiments, although upstanding gathers are not formed on the opposite end portions in the longitudinal direction of the diaper, upstanding gathers may be formed on the both or one end portion in the longitudinal direction in the absorbent article of the present invention. It is also accepted that no upstanding gathers are formed on the opposite side portions in the longitudinal direction of the absorbent article and upstanding gathers are formed only on the both or one end portion. The liquid shut-off regions may be formed only on the peripheral edge portion of the absorbent core in the both side portions or both or one end portion in the longitudinal direction of the absorbent article. The liquid shut-off regions on the topsheet 2 may be joined to other sheets than the sheet for forming an upstanding gather. In the method for manufacturing an absorbent article, the location where the liquid shut-out portions are arranged, is not particularly limited. In the obtained absorbent article, the oozing of a body liquid in the topsheet can be prevented at various locations and the anti-leak effect can be enhanced in various manners. For example, in addition to the arrangement of the liquid shut-off regions located at an area outside the periphery of the absorbent core, sealed portions similar to the liquid shut-off regions may be arranged in a lattice shape over the entire surface of the skin contacting surface of the absorbent core. Aside from the shorts type disposable diaper, the present invention can likewise be applied to a pat of an incontinent person and a sanitary napkin.

EXAMPLE 1

(1) Formation of Topsheet w/Liquid Shut-Off Region

A liquid shut-off region having a width of 5 mm was linearly formed on the under-mentioned nonwoven fabric by heat seal [seal temperature (set temperature, the same shall apply hereinafter): 160° C.] and a topsheet 2A was obtained.

| Constitution of Nonwoven Fabric | |
|---|---|
| Fiber Composition: | fiber of a core-sheath structure whose core is polyethylene-terephthalate (PET. m.p. 230° C.) and whose sheath is polyethylene (PE, m.p. 135° C.) |
| Fiber Diameter: | 2.7 (DTEX) Basis Weight: 30 g/m$^2$ |
| Method of Manufacture: | Airthrough |

(2) Making of Diaper

An absorbent core having a high absorption polymer dispersed in pulp fibers was placed on a backsheet whose central portion is twisted, and the obtained topsheet 2A is arranged on the absorbent core such that its liquid shut-off region is located outside the absorbent core at an end portion on the stomach side of the diaper. Thereafter, a hydrophobic sheet having an elastic member was fixed to the end portion on the stomach side such that its basal end is located on the end portion of the absorbent core, and a prescribed leg portion elastic member was arranged on each of the opposite left and right side portions in the longitudinal direction of the diaper. By doing so, a diaper was obtained.

EXAMPLE 2

A diaper was manufactured in the same manner as the embodiment 1 except that a liquid shut-off region was formed by changing (or resetting) the seal temperature for the heat seal to 180° C. When the seal temperature was changed to 140° C., the liquid shut-off region could not be formed. When the seal temperature was changed to 200° C., the base material strength (adequate processing suitability) was lowered and therefore, no diaper was manufactured.

EXAMPLE 3

A diaper was manufactured in the same manner as the embodiment 1 except that the nonwoven fabric is change to another nonwoven fabric having the under-mentioned constitution and the seal temperature was changed to 140° C.

| Constitution of Nonwoven Fabric: nonwoven fabric of a dual structure | |
|---|---|
| Upper Layer: | fiber-based 3.3 (DTEX), fiber length 51 (mm) basis weight 15 (g/m²) |
| Lower Layer: | fiber-based 5.5 (DTEX), fiber length 51 (mm) basis weight 15 (g/m²) |
| Fiber Composition of Upper and Lower Layers: | fiber of a core-sheath structure whose core is polypropylene (PP. m.p. 160° C.) and whose sheath is polyethylene (PE, m.p. 130° C.) |
| Method of Manufacture: | Airthrough |

EXAMPLE 4

A diaper was manufactured in the same manner as the embodiment 3 except that a liquid shut-off region was formed by changing the seal temperature for the heat seal to 160° C. When the seal temperature was changed to 120° C., the liquid shut-off region could not be formed. When the seal temperature was changed to 180° C., the base material strength (adequate processing suitability) was lowered and therefore, no diaper was manufactured.

COMPARATIVE EXAMPLE 1

A diaper was manufactured in the same manner as the embodiment 1 except that the nonwoven fabric of the embodiment 1 was used without being subjected to heat sealing.

[Performance Evaluation: Easy Leak from the Stomach Side]

Easy leak from the stomach side was evaluated in the under-mentioned manner with respect to the diapers obtained in the embodiments and in the comparative embodiment. That is to say, thirty pieces of the obtained diapers were distributed to each of 10 monitors and the number of the diapers in which the leak occurred from the stomach side, was counted. The number of the diapers in which the leak occurred from the stomach side (stomach-side leak number) was set to the total number which the ten monitors handled or used. The result is shown in Table 1.

Table 1 shows the heat seal temperature together with the results of evaluation, which was carried out in the under-mentioned manner, with respect to the restraining effect of oozing in the topsheet (the effect for preventing the migration of a body liquid through the interior of the topsheet) and the base material strength (adequate processing suitability).

[Restraining Effect of Oozing]

A sheet material for forming an upstanding gather, a topsheet and a backsheet were composited in this order through an adhesive agent (5 g/m2) and placed on an inclination plate of 10 degrees. A colored water of 10 ml was dropped on the topsheet and it was observed how the liquid penetrates through the interior of the topsheet. When the oozing was stopped at the liquid shut-off region, it was indicated by ⊚, when there was observed some traces of oozing at the seal portion but no liquid was leaked outside, it was by ◉, and when the liquid oozing was not stopped, it was indicated by X.

[Base Material Strength (Adequate Processing Suitability)]

A nonwoven fabric was cut having 100 mm in the longitudinal direction and 50 mm in width and subjected to a tensile test under the condition of 300 mm/min in rate of pulling using a Tensilon tensile test machine. Those having 30N or more on average of five pieces (or sheets) were indicated by ○.

TABLE 1

| | Heat-seal temperature (° C.) | Restraining effect of oozing | Base material strength (Adequate processing suitability) | Leak occurred from the stomach side (Number) |
|---|---|---|---|---|
| Example 1 | 160 | ○ | ○ | 4 |
| Example 2 | 180 | ⊚ | ○ | 3 |
| Example 3 | 140 | ○ | ○ | 3 |
| Example 4 | 160 | ⊚ | ○ | 4 |
| Comparative Example 1 | — | X | ○ | 9 |

It will be appreciated, as apparent from Table 1, that the disposable diapers (invented articles) of the respective embodiments, when compared with those of the comparative embodiment, are extensively reduced in number of the diapers in which the leak occurred from the stomach side and are excellent in anti-leak performance.

INDUSTRIAL APPLICABILITY

The absorbent article of the present invention is excellent in workability and anti-leak property, capable of exhibiting a sufficient anti-leak effect even in the case where a bulky topsheet is used, good in productivity and capable of being manufactured at a low cost. In particular, excellent anti-leak property can be exhibited only by processing the topsheet without using plural sheets, so that the absorbent article of the present invention can be manufactured efficiently and at a low cost.

The invention claimed is:

1. An absorbent article including a liquid-permeable topsheet, a liquid-impermeable backsheet and a liquid-retentive absorbent core having side portions interposed between said topsheet and said backsheet, said absorbent article being substantially vertically elongated and having an upstanding gather,
wherein said topsheet has a liquid shut-off region in a linear shape over the longitudinal direction, which prevents liquid migration within said topsheet beyond the liquid shut-off region, and said liquid shut-off region is located at an area outside the periphery of said absorbent core and is formed independent of a joined section between said topsheet and a sheet material for forming said upstanding gather,
wherein said topsheet is not thermally bonded to other sheet materials at said liquid shut-off region,
wherein the sheet material for forming the upstanding gather is disposed inward of the diaper from each side edge in the longitudinal direction of the diaper,
wherein a basal end of the upstanding gather is formed by joining the sheet material to the topsheet at an upper part of each side portion of the liquid-retentive absorbent core,
wherein said topsheet extends outward beyond a basal end of said upstanding gather, at least a part of an extended section of said topsheet, which is beyond the basal end of said upstanding gather, is joined to the sheet material for forming the upstanding gather, and said liquid shut-off region is located on a portion of the extended section of said topsheet where the sheet material for forming the upstanding gather joins the topsheet, and
wherein at least part of the extended section of said topsheet is joined to said backsheet.

2. The absorbent article according to claim 1, wherein said topsheet comprises a thermally fusible material, and said liquid shut-off region is formed by melting said thermally fusible material.

3. The absorbent article according to claim 1, wherein a liquid shut-off region is also located over the widthwise direction of said absorbent article at both or one of the longitudinal end portions of said absorbent article.

4. An absorbent article including a liquid-permeable topsheet, a liquid-impermeable backsheet and a liquid-retentive absorbent core having side portions interposed between said topsheet and said backsheet, said absorbent article being substantially vertically elongated and having an upstanding gather,
wherein said topsheet has a liquid shut-off region in a linear shape over the longitudinal direction, which prevents liquid migration within said topsheet beyond the liquid shut-off region, and said liquid shut-off region is located at an area outside the periphery of said absorbent core and is formed independent of a joined section between said topsheet and a sheet material for forming said upstanding gather,
wherein said topsheet is not thermally bonded to other sheet materials at said liquid shut-off region,
wherein the sheet material for forming the upstanding gather is disposed inward of the diaper from each side edge in the longitudinal direction of the diaper,
wherein a basal end of the upstanding gather is formed by joining the sheet material to the topsheet at an upper part of each side portion of the liquid-retentive absorbent core,
wherein said topsheet extends outward beyond a basal end of said upstanding gather, at least a part of an extended section of said topsheet, which is beyond the basal end of said upstanding gather, is joined to the sheet material for forming the upstanding gather, and said liquid shut-off region is located on a portion of the extended section of said topsheet where the sheet material for forming the upstanding gather joins the topsheet,
wherein at least a part of the extended section of said topsheet is joined to said backsheet, and
wherein said article does not have a waist upstanding gather, as said upstanding gather, at both or one of the longitudinal end portions of said article, and a liquid shut-off region is also located over the widthwise direction of said article at both or one of the longitudinal end portions of said absorbent article.

5. A method for manufacturing an absorbent article including a liquid permeable topsheet, a liquid impermeable backsheet and a liquid-retentive absorbent core interposed between said topsheet and said backsheet, said topsheet having a liquid shut-off region in a linear shape for preventing liquid migration within said topsheet, said method comprising preliminarily forming said liquid shut-off region at said topsheet and then arranging said topsheet at a predetermined location of said absorbent article, and said shut-off region being formed at an area outside the periphery of said absorbent core,
wherein said topsheet comprises a thermally fusible material, said liquid shut-off region is formed by melting said thermally fusible material, and
wherein said topsheet is not thermally bonded to other sheet materials at said liquid shut-off region.

* * * * *